(12) United States Patent
Nielsen et al.

(10) Patent No.: US 7,867,290 B2
(45) Date of Patent: Jan. 11, 2011

(54) SEPARATOR FILLED WITH ELECTROLYTE

(75) Inventors: Christian S. Nielsen, River Falls, WI (US); Timothy Bomstad, Inver Grove Heights, MN (US)

(73) Assignee: Medtronic, Inc., Minneapolis, MN (US)

( * ) Notice: Subject to any disclaimer, the term of this patent is extended or adjusted under 35 U.S.C. 154(b) by 68 days.

(21) Appl. No.: 12/352,134

(22) Filed: Jan. 12, 2009

(65) Prior Publication Data

US 2010/0175235 A1   Jul. 15, 2010

(51) Int. Cl.
*H01G 9/00* (2006.01)

(52) U.S. Cl. .................................... 29/25.03
(58) Field of Classification Search ................ 29/25.03
See application file for complete search history.

(56) References Cited

U.S. PATENT DOCUMENTS

| | | | |
|---|---|---|---|
| 3,303,805 A | 2/1967 | Steiner | |
| 3,493,751 A | 2/1970 | Davies et al. | |
| 3,555,369 A | 1/1971 | Yoshino | |
| 3,612,871 A | 10/1971 | Crawford et al. | |
| 3,662,178 A | 5/1972 | Caputi et al. | |
| 3,673,017 A | 6/1972 | Peterson | |
| 3,677,844 A | 7/1972 | Fleischer et al. | |
| 3,713,921 A | 1/1973 | Fleischer et al. | |
| 3,802,972 A | 4/1974 | Fleischer et al. | |
| 3,852,134 A | 12/1974 | Bean | |
| 3,883,784 A | 5/1975 | Peck et al. | |
| 4,855,049 A | 8/1989 | Toulemonde et al. | |
| 4,956,219 A | 9/1990 | Legras et al. | |
| 5,139,624 A | 8/1992 | Searson et al. | |
| 5,306,581 A | 4/1994 | Taylor et al. | |
| 5,449,917 A | 9/1995 | Clements | |
| 5,817,984 A | 10/1998 | Taylor et al. | |
| 5,821,011 A | 10/1998 | Taylor et al. | |
| 5,914,150 A | 6/1999 | Porter et al. | |
| 6,120,875 A | 9/2000 | Haumont et al. | |
| 6,184,160 B1 | 2/2001 | Yan et al. | |
| 6,219,222 B1 | 4/2001 | Shah et al. | |
| 6,801,424 B1 | 10/2004 | Nielsen et al. | |
| 6,807,048 B1 | 10/2004 | Nielsen et al. | |
| 6,842,328 B2 | 1/2005 | Schott et al. | |
| 6,855,465 B2 | 2/2005 | Yi et al. | |
| 6,995,971 B2 | 2/2006 | Norton et al. | |
| 7,081,141 B2 | 7/2006 | Hossick-Schott et al. | |
| 2004/0103526 A1 | 6/2004 | Erhardt et al. | |
| 2004/0260354 A1* | 12/2004 | Nielsen et al. | ................ 607/37 |

FOREIGN PATENT DOCUMENTS

WO        02/02185        1/2002

* cited by examiner

*Primary Examiner*—Scott B Geyer
*Assistant Examiner*—Seahvosh J Nikmanesh
(74) *Attorney, Agent, or Firm*—Carol F. Barry

(57) ABSTRACT

Methods are provided to suitably impregnate low surface energy separator materials with polar electrolyte in an electrolytic capacitor. Backfilling methods overcome the high contact angles exhibited by polar electrolytes on porous hydrophobic separators, forcing the electrolyte into the separator pores, thereby sufficiently impregnating the separator disposed between two electrodes within the capacitor assembly. Methods enable use of separators sans surfactant or surface modifications to improve wetting.

18 Claims, 1 Drawing Sheet

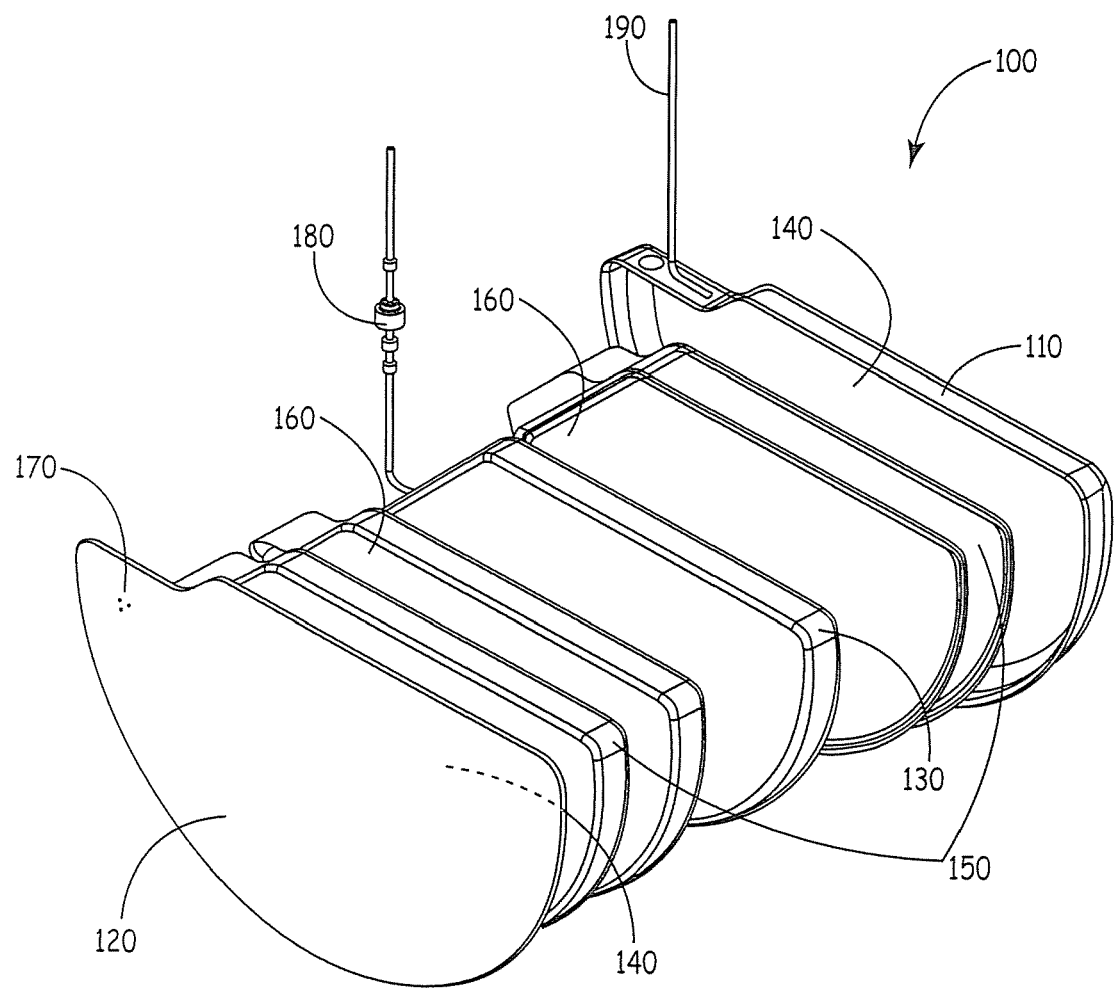

SEPARATOR FILLED WITH ELECTROLYTE

BACKGROUND

The present technology relates to electrolytic capacitors, and more particularly to methods of filling porous, hydrophobic separator materials with polar electrolytes.

Most implantable medical devices (IMDs) employ a battery, and in the case of an implantable cardiac defibrillator (ICD), also a capacitor bank including one or more high voltage electrolytic capacitors. These capacitors may each have an operating voltage ranging from about 200 to 400 V. Such operating requirements have generally necessitated use of wet electrolytic technology that in turn requires a mechanical separator system to ensure the separation of electrodes of opposite polarity; i.e., cathode and anode. The separators employed in these electrochemical cells are typically of such construction that they are wettable with whatever liquid electrolyte is used in the electrochemical cell.

In the case of some electrochemical cells, notably advanced valve metal (AVM) capacitors, the liquid electrolyte is comprised in part of a very polar constituent that causes the electrolyte to exhibit a high wetting angle on relatively hydrophobic materials often used as separators. For example, if the polar liquid electrolyte is attracted to the separator surface, such as water on a strongly hydrophilic surface, the droplet will spread out on the solid surface and the contact angle will be close to 0°. Hydrophilic separator materials are hence readily wetted by polar electrolytes. Conversely, a less hydrophilic separator will have a contact angle up to 90°, and highly hydrophobic surfaces may have contact angles as high as 150°, or even nearly 180°. On these hydrophobic surfaces, polar electrolyte droplets simply rest on the surface, without actually wetting the separator material to any significant extent. These surfaces are termed super-hydrophobic, and include for example, fluorinated materials (e.g., Teflon® and Teflon®-like coatings) that may be micro-patterned and/or that are micro-porous.

A substrate material for use in an electrochemical cell is preferably chemically inert and structurally stable. Materials exhibiting these properties include hydrophobic materials having low surface energies, such as the aforementioned fluorinated materials. While such materials may be advantageously nonreactive with components of the polar electrolyte, such as acids and/or various solvents, these materials are nevertheless difficult to wet with a polar electrolyte. Wetting of a hydrophobic substrate with a polar electrolyte has been facilitated by using one or more surfactants and/or surface energy modifications of the substrate material. However, alternative approaches that promote impregnation of polar electrolyte into porous, hydrophobic separator materials are desirable.

SUMMARY

The present technology includes systems, methods, articles, and compositions that relate to backfilling capacitor assemblies.

An electrochemical cell, such as a capacitor assembly, includes at least one pair of electrodes and a porous separator disposed between the electrodes. The capacitor assembly may be sealed from the exterior atmosphere except via at least one fill-port. Backfilling the capacitor assembly includes using vacuum to evacuate the interior atmosphere of the capacitor assembly. The fill-port may be coupled to a reservoir of liquid electrolyte and pressure may be applied to the reservoir of liquid electrolyte, forcing the liquid electrolyte into the evacuated capacitor assembly through the fill-port. The fill-port can then be sealed.

DRAWINGS

The drawings described herein are for illustrative purposes only of selected embodiments and do not represent all possible implementations, and are not intended to limit the scope of the present disclosure.

FIG. 1 illustrates an exploded, perspective view of one embodiment of a capacitor assembly configured for vacuum backfilling according to the present methods.

DETAILED DESCRIPTION

The following description of technology is merely exemplary in nature of the subject matter, manufacture and use of one or more inventions, and is not intended to limit the scope, application, or uses of any specific invention claimed in this application or in such other applications as may be filed claiming priority to this application, or patents issuing therefrom. The following definitions and non-limiting guidelines must be considered in reviewing the description of the technology set forth herein.

The headings (such as "Background" and "Summary") and sub-headings used herein are intended only for general organization of topics within the present disclosure, and are not intended to limit the disclosure of the technology or any aspect thereof. In particular, subject matter disclosed in the "Introduction" may include novel technology and may not constitute a recitation of prior art. Subject matter disclosed in the "Summary" is not an exhaustive or complete disclosure of the entire scope of the technology or any embodiments thereof. Classification or discussion of a material within a section of this specification as having a particular utility is made for convenience, and no inference should be drawn that the material must necessarily or solely function in accordance with its classification herein when it is used in any given composition.

The citation of references herein does not constitute an admission that those references are prior art or have any relevance to the patentability of the technology disclosed herein. All references cited in the "Detailed Description" section of this specification are hereby incorporated by reference in their entirety.

The description and specific examples, while indicating embodiments of the technology, are intended for purposes of illustration only and are not intended to limit the scope of the technology. Moreover, recitation of multiple embodiments having stated features is not intended to exclude other embodiments having additional features, or other embodiments incorporating different combinations of the stated features. Specific examples are provided for illustrative purposes of how to make and use the apparatus and systems of this technology and, unless explicitly stated otherwise, are not intended to be a representation that given embodiments of this technology have, or have not, been made or tested.

As referred to herein, all compositional percentages are by weight of the total composition, unless otherwise specified. As used herein, the word "include," and its variants, is intended to be non-limiting, such that recitation of items in a list is not to the exclusion of other like items that may also be useful in the materials, compositions, devices, and methods of this technology. Similarly, the terms "can" and "may" and their variants are intended to be non-limiting, such that recitation that an embodiment can or may comprise certain elements or features does not exclude other embodiments of the present technology that do not contain those elements or features.

"A" and "an" as used herein indicate "at least one" of the item is present; a plurality of such items may be present, when possible. "About" when applied to values indicates that the calculation or the measurement allows some slight imprecision in the value (with some approach to exactness in the value; approximately or reasonably close to the value; nearly). If, for some reason, the imprecision provided by "about" is not otherwise understood in the art with this ordinary meaning, then "about" as used herein indicates at least variations that may arise from ordinary methods of measuring or using such parameters. In addition, disclosure of ranges includes disclosure of all distinct values and further divided ranges within the entire range.

The present technology relates to backfilling methods for wetting a low surface energy separator with a polar electrolyte. Backfilling, or forced-filling methods, make it possible to form necks of electrolyte through porous separator membranes allowing for an electrochemical cell (e.g., AVM type capacitor) to function without any surfactant or other surface energy modifications. The present methods simplify capacitor assembly and design by eliminating surfactants or other surface energy modification on the porous separator material(s) used in electrochemical cells where a polar (i.e., high wetting angle) electrolyte may be used. This allows for separator materials to be used "as is," without any pretreatments, in construction of capacitor assemblies. Furthermore, additional materials and suppliers may be considered for electrochemical cell applications (e.g., capacitors, batteries, etc.). For example, highly hydrophobic and porous materials constructed of fluoropolymers can be suitably wetted by polar solvents by the present methods. In addition, mechanical advantages may be realized in using sintered materials that are typically not surface modified. Cost savings are possible since some base materials (e.g., PTFE, polypropylene, etc.) are available as filter materials and/or non-surface (or bulk) modified membranes.

A capacitor assembly typically comprises an anode having a dielectric layer, a separator, a cathode, and an electrolyte solution. The anode and cathode often comprise stacked or coiled metallic foil members although pressed, sintered and formed powdered metal anodes are known and used in the art. The energy of a capacitor assembly may be stored in the electromagnetic field generated by opposing electrical charges separated by the dielectric layer disposed on the surface of the anode. Etching may be used to increase the surface area of the anode, as the energy stored by the cell may be proportional to the surface area of the anode. A dielectric oxide layer may be formed on the anode when a voltage is applied in an electrolytic solution. The dielectric layer insulates the anode from the cathodic electrolytic solution, allowing charge to accumulate. The separator holds the anode and cathode foils or powdered slug-type anodes apart to maintain charge and prevent short-circuiting.

The following references include features suitable for use and/or recognizable by a person of ordinary skill in the art as adaptable for use in the present capacitors and methods. U.S. Pat. No. 7,081,141 discloses electrolytic capacitors and electrolytes. U.S. Pat. No. 6,995,971 to Norton et al. discloses capacitor cells and separators that are impregnated with a surfactant or that absorb and/or interact with a surfactant. U.S. Pat. No. 6,842,328 to Schott et al. discloses capacitors, a capacitor bank that includes a plurality of capacitors, and capacitance-enhancing materials. U.S. Pat. No. 6,807,048 to Nielsen et al. discloses electrolytic capacitor structures. U.S. Pat. No. 6,219,222 to Shah et al. discloses tantalum-based capacitors. U.S. Pat. No. 6,184,160 to Yan et al. discloses flat electrolytic capacitors and anode/cathode sub-assemblies and incorporation thereof into implantable medical devices such as implantable cardiac defibrillators (ICDs).

The anode and cathode layers can be comprised of any electrically conductive anode and cathode material known in the art to be used in capacitor cells. For example, typical anode materials include alkali metals or alkali earth metals selected from Groups IA, IIA and IIIB from the Periodic Table of Elements. For example, these anode materials include lithium, aluminum, sodium, potassium, calcium, magnesium, vanadium, tantalum, niobium, alloys thereof, and combinations thereof. In some embodiments, the anode may be a valve metal chosen from titanium, tungsten, chromium, aluminum, zirconium, hafnium, zinc, vanadium, niobium, tantalum, bismuth, antimony, and mixtures and alloys thereof. Tantalum is a preferred anode.

In some embodiments, the anode comprises capacitor grade tantalum powder, such as the "NH" family of powders, pressed or molded into the desired shape. These tantalum powders have a charge per gram rating of between approximately 17,000 to 23,000 microfarad-volts/gram and have been found to be well suited for implantable cardiac device capacitor applications. Tantalum powders of this type are commercially available from HC Starck, Inc. located in Newton, Mass.

Tantalum powder may be mixed with approximately 0 to 5 percent of a binder, such as ammonium carbonate, when forming an anode. Use of one or more binders can facilitate metal particle adhesion and die lubrication during pressing. The powder and binder mixture are dispended into a die cavity and are pressed to a density of approximately 4 grams per cubic centimeter to approximately 8 grams per cubic centimeter. After pressing, it may be beneficial to modify anode porosity to improve conductivity within the internal portions of the anode. Porosity modification has been shown to significantly reduce resistance. Macroscopic channels are incorporated into the body of the anodes to accomplish this. Binder may then be removed from the anodes either by washing in warm deionized water or by heating at a temperature sufficient to decompose the binder. Complete binder removal may be desirable since residuals may result in high leakage current. Washed anodes are then vacuum-sintered at between approximately 1,350 degrees centigrade and approximately 1,600 degrees centigrade to permanently bond the metal anode particles.

An oxide may be formed on the surface of the sintered anode by immersing the anode in an electrolyte and applying a current. The electrolyte includes constituents such as water and phosphoric acid and perhaps other organic solvents. The application of current drives the formation of an oxide film that is proportional in thickness to the targeted forming voltage. A pulsed formation process may be used wherein current is cyclically applied and removed to allow diffusion of heated electrolyte from the internal pores of the anode plugs. Intermediate washing and annealing steps may be performed to facilitate the formation of a stable, defect-free oxide.

Typical cathode materials include electrically conductive metals such as ruthenium, vanadium, copper, silver, chromium, bismuth, lead, tantalum, carbon, aluminum, magnesium, titanium, niobium, zirconium, zinc, and alloys and combinations thereof. These types of cathode materials may be provided with a semi-conductive or metal-like conductive coating. The coating can be carbon or an oxide, nitride, carbide, or carbon nitride of a metal. Suitable cathode metals further include tantalum, titanium, nickel, iridium, platinum, palladium, gold, silver, cobalt, molybdenum, ruthenium, manganese, tungsten, iron, zirconium, hafnium, rhodium, vanadium, osmium, and niobium. A preferred cathode electrode comprises a porous ruthenium oxide film provided on a titanium substrate. Other cathode materials include graphite or glassy carbon on titanium carbide, carbon and silver vanadium oxide on titanium carbide, carbon and crystalline manganese dioxide on titanium carbide, platinum on titanium, ruthenium on titanium, barium titanate on titanium, carbon and crystalline ruthenium oxide on titanium carbide, carbon and crystalline iridium oxide on titanium carbide, silver vanadium oxide on titanium, and the like.

In some embodiments, the encasement of the capacitor itself may serve as the cathode electrode. This may be accomplished by depositing cathode material on an inner wall of the encasement; or, if cathode material is deposited on one or more substrates, by electrically connecting the substrates to the encasement. Alternatively, the encasement may be made electrically neutral by not coupling the cathode(s) to the encasement. The cathode may simply be sealed within separators. In this situation, however, it may be necessary not only to provide access to an anode electrode at the exterior of the encasement but provisions must also be made to access the cathode electrode from the exterior of the capacitor. For example, various approaches have involved the use of separate feedthroughs including ferrules and insulators.

The anode, separator, and cathode of the capacitor cell can be configured together in any suitable form. For example, the anode, separator, and cathode material can be configured together as strips laminated together. In other embodiments, the anode, separator, and cathode material can be configured as separate layers of material. Configurations include those illustrated in U.S. Pat. No. 6,995,971 to Norton et al. and U.S. Pat. No. 6,842,328 to Schott et al. discloses suitable electrodes and methods for producing electrodes.

Electrodes may be coupled to electrically conductive wires and feedthrough assemblies as known in the art, including those described in U.S. Pat. Nos. 6,855,465; 5,817,984; 5,821,011; and 5,306,581 all to Taylor et al.

The separator material physically separates the anode(s) and cathode(s) from each other and prevents electrical short circuits between the electrodes. The separator material may preferably be unreactive with the anode, cathode, and electrolyte and may be sufficiently porous to allow the electrolyte to freely flow through the separator. The separator may provide structural integrity to maintain the distance between electrodes upon compression, for example, when one or more electrode layers are pressed in forming a capacitor.

Separators may be formed from a material that: (a) is chemically inert; (b) is chemically compatible with the selected electrolyte; (c) may be impregnated with the electrolyte to produce a low resistance ionic path between adjoining anode and cathode layers; and (d) physically separates adjoining anode and cathode layers. Separators utilized in embodiments of the present disclosure may also be formed of woven and non-woven materials such as cellulose, paper, porous polymeric materials, and fabric or gauze materials. For example, porous polymeric materials may be disposed between anode and cathode layers, similar to those described in U.S. Pat. Nos. 3,555,369 to Yoshino and 3,883,784 to Peck et al.

The separator may be produced from any suitable material, including: 1) nonwoven polymers, such as polyesters, polystyrenes, aromatic polyesters, polycarbonates, polyolefins, including polyethylene, polyethylene terephthalate, polypropylene, vinyl plastics such as polyvinyl difluoride (PVDF), and cellulose esters such as cellulose nitrate, cellulose butyrate and cellulose acetate; 2) micro-porous polymers such as polytetrafluoroethylene (PTFE), including expanded polytetrafluoroethylene (ePTFE); 3) track-etched materials; and 4) papers, such as Kraft paper (cellulose) or Manila paper. Suitable micro-porous polymer separator materials include ePTFE of the type produced by W.L. Gore, Inc. located in Elkton, Md. or polypropylene of the type produced by Celgard, Inc. located in Charlotte, N.C.

The separator may be a track-etched material. The process of making track-etched materials is known in the art and many variations of the process exist. Examples of processes for forming track-etched materials are disclosed in U.S. Pat. Nos. 3,303,805; 3,493,751; 3,612,871; 6,120,875; 3,662,178; 3,673,017; 3,677,844; 3,713,921; 3,802,972; 3,852,134; 4,855,049; 4,956,219; 5,139,624; 5,449,917; and 5,914,150, the entire contents of each of which are incorporated herein by reference. The present separator can be comprised of any material that has been track-etched according to any of the processes disclosed in the references above or according to any known track-etching process. Track-etched separator materials include polymeric materials, such as polyesters, polystyrenes, aromatic polyesters, polycarbonates, polyolefins, including polyethylene, polyethylene terephthalate, polypropylene, vinyl plastics such as polyvinyl difluoride (PVDF), and cellulose esters such as cellulose nitrate, cellulose butyrate and cellulose acetate.

In some embodiments, the track-etched material comprises a polycarbonate material. Such polycarbonate materials have outstanding impact resistance and toughness and also have high tensile and structural strength. Commercial polycarbonate materials include those having the trademarks Lexan™, Merlon™, Makraylon™, Jupilon™, and Panlite™. Additionally, commercially available track-etched membranes include those having the trademarks Nuclepore™ and Cyclopore™ distributed by Whatman, Inc. located in Newton, Mass., Isopore™ distributed by Millipore, Inc. located in Billerica, Mass., Poretics™ and Memtrex™ distributed by Osmonics located in Minnetonka, Minn., and SPI-Pore™ distributed by Structure Probe, Inc. located in West Chester, Pa.

In some embodiments, the separator may be a pure cellulose, very low halide or chloride content Kraft paper, having a thickness of about 0.0005 inches, a density of about 1.06 grams/cm.sup.3, a dielectric strength of 1,400 ac Volts per 0.001 inches thickness, and a low number of conducting paths (about $0.4/ft^2$ or less). When including either anode foil plates or cathode foil plates in conjunction with separators, the separators are preferably cut slightly larger than the foil plates to accommodate misalignment during the stacking of separators and foil plates and to prevent subsequent shorting between electrodes of opposite polarity.

The separator material has a thickness suitable for use in a capacitor cell. The range of thicknesses of separators typically available for utilization in capacitor cells can be about 250 microns or less and some embodiments are between about 5 to about 250 microns (or approximately 0.0002-0.01 inches), including about 10 to about 50 microns.

The present capacitors and methods do not require surfactant and/or modifications to the separator material in order to improve the wettability and increase the separator's electrolyte absorption characteristics. For example, modifications such as surface treatments and/or texturing used to increase the wettability of the separator are not required. Nor do the present capacitors and methods require one or more surfactants embedded in or associated with the separator to enhance the wettability of the separator. For example, the present capacitors and methods may advantageously forgo surfactants, such as those described in U.S. Pat. No. 6,995,971 to Norton et al., to simplify capacitor manufacture.

The separator may be wetted and/or saturated with a liquid electrolyte. Electrolytes including water are typically known as polar electrolytes. The electrolyte may be a conductive liquid having a high breakdown voltage that may be comprised of water, organic solvents, and weak acids, or comprised of water, organic solvents, and sulfuric acid. Liquid electrolyte saturates or wets the separator layer(s) disposed between the electrodes. In some embodiments, the electrolyte may include a polyol, such as glycerol or a glycol, as these render the capacitor operative over an increased temperature range. For example, the electrolyte solution may contain ethylene glycol and/or tetraethylene glycol dimethyl ether ("tetraglyme"). Suitable electrolytes include those described in U.S. Pat. No. 7,081,141 to Hossick-Schott et al. The capacitor assembly may include any electrolyte solution suitable for use with a capacitor.

The present disclosure provides methods for making an electrolytic capacitor. Methods generally comprise providing a separator and positioning on the separator one or more pairs of alternating cathode and anode plates or layers so that a separation is maintained between the anode and cathodes. The separator may be impregnated and/or absorbed with a surfactant, as described in U.S. Pat. No. 6,995,971 to Norton et al.; however, the present backfill methods do not require the use of a surfactant in order to facilitate drawing of electrolyte into the separator. In positioning the separator within the cell, it is important to maintain contact and alignment of all anode, cathode, and separator components. Failure in these aspects may lead to short-circuiting or inefficient capacitor performance. The anode-separator-cathode assembly may then be sealed or enclosed in a case and backfilled with one or more suitable electrolytes.

After assembly and sealing of the capacitor, an electrolyte may be introduced into the casing via vacuum through one or more fill-ports by using a backfilling method. The fill-port provides a route for liquid electrolyte to enter into the capacitor to impregnate the separator(s) positioned between the electrodes. Backfilling may be performed by placing the capacitor in a vacuum chamber, evacuating the interior of the capacitor, and coupling the fill-port to a reservoir of liquid electrolyte. When the chamber is evacuated, pressure is reduced inside the capacitor. When the vacuum is released, pressure inside the capacitor re-equilibrates and liquid electrolyte is drawn through the fill-port(s) into the capacitor. The fill-port may then be sealed, for example, using a plug, adhesive, weld, or other sealing means.

In some embodiments, one or more fill-ports and capillaries may be employed in the backfilling method. For example, the fill-port may be coupled to the interior of the capacitor via a capillary. The fill-port may also be coupled to one or more capillaries that travel to multiple separators. The capillary may be positioned to maximize impregnation of the separator, for example, by delivering liquid electrolyte directly to a portion of the separator, such as the center of the separator. In this manner, the separator fills with liquid electrolyte first and any residual gas or bubble that remains within the electrolyte-filled capacitor is not located within or at the separator. Residual gas or bubbles positioned within or at anode-separator-cathode layers may interfere with the capacitor's function. After the capacitor is filled with liquid electrolyte, the fill-port may be sealed.

Fill-ports and capillaries may be positioned on the capacitor case or outer seal parallel and/or perpendicular to the electrode-separator layers. Where the fill-port is located on a surface parallel to the electrode-separator layers, a capillary coupled to the fill-port may traverse one or more electrodes and/or separators to deliver electrolyte. For example, a capillary may traverse multiple electrodes and separators and have an exit port at or within each separator layer in order to fill each separator layer. In one embodiment, a capacitor assembly includes at least two fill-ports, where the fill-ports are spaced on the capacitor case at or near the greatest linear distance possible from each other. For example, the two fill-ports may be on opposite corners of a capacitor assembly.

In some embodiments, the capacitor may be filled with electrolyte using the following backfilling method. The capacitor and liquid electrolyte are introduced into a vacuum chamber, the vacuum chamber is evacuated with the capacitor interior being evacuated through the fill-port at the same time, the fill-port is subsequently coupled or contacted to the liquid electrolyte, and the evacuated container is allowed to equilibrate with atmospheric pressure or is charged with greater than atmospheric pressure (i.e., super-atmospheric pressure), thereby forcing liquid electrolyte through the fill-port and into the evacuated capacitor.

In the case where two capillaries are provided, the first capillary can be coupled to a vacuum source, for example via fittings and/or flange elements known from high-pressure liquid chromatography, and the other capillary can be coupled to a reservoir of liquid electrolyte. In this case, the capacitor interior is evacuated using the vacuum source where evacuated space is replaced with the liquid electrolyte. For example, either the liquid electrolyte is drawn into the capacitor by means of vacuum or alternatively, if the reservoir of liquid electrolyte is in the form of an injection syringe, the liquid electrolyte may be injected into the evacuated capacitor. Injection using such a syringe may be performed using pressure greater than the pressure differential established by the evacuated capacitor; e.g., super-atmospheric pressure. The capillary opening on the capacitor side where which the evacuation is carried out may be in the vicinity of the highest point of the capacitor so that the residual volume after flooding of the capillary entrance is as small as possible.

The pressure and size of the empty volume remaining determines the size of any gas bubble remaining in the capacitor assembly. In vacuum backfilling, where gas is no longer being removed from the evacuated capacitor during introduction of the liquid electrolyte, all the gas corresponding to residual pressure within the evacuated cell remains inside the capacitor assembly. If the volume of the gas bubble is sufficiently small, the bubble may dissolve in the liquid electrolyte. In order to improve the dissolution capacity of the liquid electrolyte for dissolving any remaining gas bubble, the liquid electrolyte may be degassed by vacuum treatment before introduction into the capacitor.

In some embodiments, the backfilling method may include re-evacuating the capacitor after an initial vacuum backfilling. The same fill-port and/or capillary may be used in re-evacuating the capacitor as was used during the initial backfilling, or a different fill-port and/or capillary may be used. For example, a second fill-port and/or capillary may be positioned opposite from the initial or first fill-port and/or capillary to evacuate trapped gas or a bubble remaining to the far side of the initial backfill. Re-evacuating the capacitor causes residual gas or a bubble, and possibly some liquid electrolyte, to be conveyed out of the capacitor. The re-evacuated capacitor is then allowed to again backfill with liquid electrolyte, reducing or even eliminating the residual gas remaining in the capacitor in accordance with the ratio between the total chamber volume and the vacuum volume of the second evacuation.

In some embodiments, the backfilling method includes placing the capacitor in a vacuum chamber along with a reservoir or container (e.g., a dish or small cup) of the liquid electrolyte. This vacuum chamber is generally evacuated under a vacuum of about 1 mm Hg or lower and the fill-port on the capacitor is then lowered into the container, just beneath the surface of the media. The vacuum chamber is then vented to atmospheric pressure; e.g., using air, nitrogen, or some other inert gas. The liquid electrolyte is forced into the capacitor until it is filled. Once filled, the fill-port is sealed or plugged.

In some embodiments, the liquid electrolyte may have inherently high viscosity and low vapor pressure. To fill with liquid electrolyte using the vacuum backfill method, elevated temperatures may be used so that the liquid electrolyte viscosity is sufficiently lowered so that the material may flow into and fill the capacitor. Because of inherently low vapor pressure of such liquid electrolytes, even at elevated temperatures, void space such as gas or bubbles may not a significant problem during backfilling.

In some embodiments, the backfilling method includes the following features. An implantable medical device is provided comprising a sealed or encased capacitor having a fill-port, or a fill-port is introduced into the outer case, so that the fill-port, for example with an associated capillary, traverses the outer case to the interior of the capacitor. To vacuum backfill the device, liquid electrolyte can be filled through the fill-port. Once inside the device, the liquid electrolyte impregnates one or more separators located between electrodes. The fill-port may be small making it easier to seal the fill-port once the device is full so that no leaks occur through the fill hole. However, when a small fill-port is used (e.g., less than about 1 mm×1 mm×150 microns) it is difficult to fill the device, for example, by using a hypodermic needle or the like. Also, when there is only one fill-port, back pressure impedes complete filling through the one fill-port. Thus, vacuum backfilling provides a means to fill such a device.

To vacuum backfill, the empty device is placed in a vacuum chamber along with a reservoir of the liquid electrolyte intended to be filled through the fill-port into the device. The vacuum chamber is evacuated to a high vacuum; e.g., 1 mmHg or better. Means are then used to lower the fill-port just under the surface of the liquid electrolyte. The vacuum chamber is now vented to atmospheric pressure (typically using nitrogen or similar inert gas). Atmospheric pressure forces the liquid electrolyte into the device and so fills it. However, how completely it fills is a function both of the vacuum pressure upon evacuation and the atmospheric pressure to which the chamber is vented during venting.

Although a vacuum pump can evacuate the vacuum chamber to $10^{-6}$ mm Hg or better, the vapor pressure of the liquid electrolyte may limit how high a vacuum can be achieved. This is because the vacuum pump can reduce the pressure down to the vapor pressure (at the temperature of the chamber) of the liquid electrolyte used. For example, once the pressure equals the vapor pressure, pressure will go no lower until one or more components of the liquid electrolyte have evaporated. Thus the choice of liquid electrolyte components, including solvents, through their vapor pressure, can dictate how large a bubble will remain after backfilling a given device volume. As the device interior volume increases the problem may get worse, and unless a sufficiently low vapor pressure solvent is chosen, or unless means such as cooling the fluid and chamber (to reduce vapor pressure) or over-pressuring during backfill (to force more fluid in) are employed, an unacceptable amount of residual gas or a bubble will be left within the device. While a small bubble may dissolve into the liquid electrolyte over time, a larger bubble will not completely disappear. Further, if the viscosity of the liquid electrolyte to be filled is very high, then it may be difficult to fill at room temperature.

If higher filling temperatures are used, the residual bubble may be larger as the vapor pressure increases with temperature; i.e., $P_A V_A = P_V V_V$, where $P_A$=pressure to which the chamber is finally vented; $V_A$=volume of gas trapped in the cell after completely filling the cell; $P_V$=pressure in the chamber after evacuation and prior to filling; and $V_V$=volume of the empty device, i.e., capacitor void volume. Undissolved gas trapped in the device after incomplete filling will usually form a bubble. The device may be over-pressured, for example to several atmospheres or more, after filling if it is desired to fill more completely.

Note that if two or more solvents are mixed together to form an ideal solution in the liquid electrolyte, the vapor pressure of the solution is simply the sum of the vapor pressures of each component. Solvents with low vapor pressures are better choices for use as solvent components in electrolyte solutions for vacuum backfilling. This becomes more important when the device interior volume is increased, for example, when the device includes multiple capacitors such as a capacitor bank. Concentrations and types of electrolyte solutes may alter the vapor pressure of the electrolyte, typically by depressing the vapor pressure. Lower boiling point solvents tend to have relatively high vapor pressures at room temperature. Thus, higher boiling point solvents, which tend to have lower vapor pressures at room temperature, are more suitable for the vacuum backfilling method and tend to leave smaller bubbles in the filled device.

The present backfill methods and capacitors and devices produced thereby can be integrated with the methods of making and using implantable medical devices as described in U.S. Pat. No. 6,184,160 to Yan et al.

The present technology provides several benefits and advantages. The present systems and methods improve manufacture of capacitor assemblies by providing a means to impregnate low surface energy separator material with polar electrolytes without having to prepare or modify the separator material. For example, no surface modifications and/or surfactant are necessary in order for the liquid, polar electrolyte to penetrate the porous separator. Separators made from sheets of porous polypropylene or ePTFE can be used "as is" from a manufacturer or supplier, saving time and cost.

Example

Referring now to FIG. 1, a capacitor assembly 100 for backfilling with polar electrolyte is shown. The capacitor assembly 100 has a titanium can 110 that is sealable with a titanium cover 120 and closure of fill ports 170. A tantalum electrode 130 serves as an anode while a coating 140 on the interior of the titanium can 110 serves as a cathode. The tantalum electrode 130 is flanked by porous ePTFE separators 150 and polypropylene separators 160. The porous separators 150, 160 are not surface-modified and are not embedded with surfactant. A fill-port 170 comprises three holes that pass through the titanium cover 120. A feedthrough assembly 180 is electrically connected to the tantalum electrode 130 and passes outside the capacitor assembly 100, the feedthrough assembly 180 being sealed and insulated in traversing the titanium can 110. A conductive wire 190 is electrically connected to the titanium can 110 enabling a cathode contact.

The capacitor assembly 100 components are layered, aligned, and the titanium cover 120 is hermetically sealed to the titanium can 110. The feedthrough assembly 180 also provides a hermetic seal in traversing the titanium can 110. In this way, the only fluid connection between the interior and exterior of the capacitor assembly 100 is via the fill-port 170. The capacitor assembly 100 is then subjected to vacuum to evacuate the interior atmosphere through the fill-port 170, including the void volumes of the porous separators 150, 160.

Once the desired vacuum is obtained, the fill-port 170 is contacted with a reservoir of degassed liquid polar electrolyte (not shown). Atmospheric pressure is slowly restored to the reservoir of degassed liquid polar electrolyte, forcing the polar electrolyte through the fill-port 170 and into the evacuated and sealed capacitor assembly 100 interior. The vacuum within the capacitor assembly is then replaced by the polar electrolyte, and in particular, the polar electrolyte is forced into the void volumes of the porous separators 150, 160, effectively filling the pores of the hydrophobic ePTFE separators 150 and polypropylene separators 160. Thus, the pressure differential employed in the backfilling method overcomes the low surface energy surfaces of the separators 150, 160 causing the polar electrolyte to penetrate the pores, wetting the separators 150, 160, thereby providing conductive paths between the tantalum electrode 130 (anode) and the titanium can 110 (cathode). The fill-port 170 is then hermetically sealed.

Those of skill in the art will recognize that many of the embodiments and techniques provided by the present technology may be used, as applicable, as electrolytic capacitors for diverse electrochemical cells, such as primary and secondary battery cells. That is, the present teachings are not limited to capacitor cells but should be fairly construed to include other types of electrochemical cells, such as batteries, etc. In addition, the embodiments and the examples described herein are exemplary and not intended to be limiting in describing the full scope of apparatus, systems, and methods of the present technology. Equivalent changes, modifications and variations of some embodiments, materials, compositions and methods can be made within the scope of the present technology, with substantially similar results.

What is claimed is:

1. A method of backfilling a capacitor assembly comprising:
    (a) evacuating the interior of a capacitor assembly, the capacitor assembly comprising at least two electrodes and a micro-porous separator disposed between the electrodes, the capacitor assembly sealed from the exterior atmosphere except via at least one fill-port,
        wherein the micro-porous separator is free of surfactant and not surface modified to increase wettability;
    (b) coupling the fill-port to a reservoir of liquid electrolyte, where the pressure on the liquid electrolyte is greater than the interior pressure of the evacuated capacitor assembly, thereby forcing the liquid electrolyte into the evacuated capacitor assembly through the fill-port.

2. The method of claim 1, further comprising: (c) sealing the fill-port.

3. The method of claim 1, wherein evacuating an interior atmosphere of a capacitor assembly reduces the pressure inside the capacitor assembly to about 1 mmHg or less.

4. The method of claim 1, wherein the interior of the capacitor assembly is evacuated to less than atmospheric pressure and the pressure on the liquid electrolyte is atmospheric pressure.

5. The method of claim 1, wherein the pressure on the liquid electrolyte is super-atmospheric.

6. The method of claim 1, wherein at least one of the electrodes comprises tantalum.

7. The method of claim 1, wherein the porous separator comprises a member of the group selected from polyesters, polystyrenes, aromatic polyesters, polycarbonates, polyolefins, polyethylene, polyethylene terephthalate, polypropylene, vinyl plastic, polyvinyl difluoride, cellulose ester, cellulose nitrate, cellulose butyrate, cellulose acetate, polytetrafluoroethylene, expanded polytetrafluoroethylene, and combinations thereof.

8. The method of claim 1, wherein the liquid electrolyte is a polar electrolyte.

9. The method of claim 8, wherein the polar electrolyte comprises water, a polyol, and an acid.

10. The method of claim 1, wherein the liquid electrolyte is degassed prior to applying pressure to the reservoir of liquid electrolyte and forcing the liquid electrolyte into the evacuated capacitor assembly.

11. The method of claim 1, wherein the liquid electrolyte is heated prior to applying pressure to the reservoir of liquid electrolyte and forcing the liquid electrolyte into the evacuated capacitor assembly.

12. The method of claim 1, wherein the fill-port comprises at least one capillary.

13. The method of claim 1, wherein the fill-port comprises a capillary running to the separator.

14. The method of claim 1, wherein the capacitor assembly comprises a capacitor bank having a plurality of electrode pairs, each electrode pair having a porous separator disposed in-between.

15. The method of claim 1, wherein the capacitor assembly comprises a portion of an implantable cardiac defibrillator.

16. A method of backfilling a capacitor assembly comprising:
    (a) evacuating the interior atmosphere of a capacitor assembly using vacuum, the capacitor assembly comprising a pair of electrodes and a porous separator disposed between the electrodes, the capacitor assembly sealed from the exterior atmosphere except via at least one fill-port,
        wherein the porous separator is free of surfactant and not surface modified to increase wettability;
    (b) coupling the fill-port to a reservoir of liquid electrolyte;
    (c) applying pressure to the reservoir of liquid electrolyte, thereby forcing the liquid electrolyte into the evacuated capacitor assembly through the fill-port;
    (d) re-evacuating the interior of the capacitor assembly to remove any volume of residual gas; and
    (e) replacing the volume of residual gas with liquid electrolyte.

17. The method of claim 16, wherein the capacitor assembly further comprises a second fill-port located at or substantially at the greatest linear distance possible from the fill-port used in steps (a), (b), and (c); and re-evacuating the interior of the capacitor assembly to remove any volume of residual gas uses the second fill-port.

18. A method of backfilling a capacitor assembly comprising:
    (a) evacuating the interior atmosphere of a capacitor assembly using vacuum, the capacitor assembly comprising:
        at least one pair of electrodes, at least one of the electrodes comprising tantalum; and
        a porous separator disposed between the electrodes, the porous separator comprising a hydrophobic polymer and the porous separator is free of surfactant and not surface modified to increase wettability;
    wherein, the capacitor assembly is sealed from the exterior atmosphere except via at least one fill-port;
    (b) coupling the fill-port to a reservoir of liquid, polar electrolyte, the liquid electrolyte comprising water and an acid; and
    (c) applying pressure to the reservoir of liquid, polar electrolyte, thereby forcing the liquid, polar electrolyte into the evacuated capacitor assembly through the fill-port; and
    (d) sealing the fill-port.

* * * * *